US005811365A

United States Patent [19]
Barry

[11] Patent Number: 5,811,365
[45] Date of Patent: Sep. 22, 1998

[54] ZINC OXIDE COMPOSITION FOR USE IN CATALYSTS

[75] Inventor: Nay Barry, Surrey, United Kingdom

[73] Assignee: The British Petroleum Company, p.l.c., London, England

[21] Appl. No.: 826,576

[22] Filed: Apr. 2, 1997

Related U.S. Application Data

[63] Continuation of Ser. No. 446,786, filed as PCT/GB93/02479, Dec. 02, 1993, abandoned.

[30] Foreign Application Priority Data

Dec. 4, 1992 [GB] United Kingdom ............ 9225372

[51] Int. Cl.$^6$ .............. B01J 23/06; B01J 23/80
[52] U.S. Cl. .............. 502/343; 502/329; 502/341; 502/342
[58] Field of Search .............. 502/340, 341, 502/342, 343, 329, 328

[56] References Cited

U.S. PATENT DOCUMENTS

| | | | |
|---|---|---|---|
| 4,039,302 | 8/1977 | Khera | 48/197 R |
| 4,107,091 | 8/1978 | Khera | 252/466 J |
| 4,172,813 | 10/1979 | Feinstein et al. | 585/475 |
| 4,199,479 | 4/1980 | Wikles | 252/457 |
| 4,340,745 | 7/1982 | Dockner et al. | 548/347 |
| 4,638,085 | 1/1987 | Broecker et al. | 560/208 |
| 4,729,889 | 3/1988 | Flytani-Stephanopoulos et al. | 423/593 |
| 4,977,123 | 12/1990 | Flytzani-Shephanopoulos et al. | 502/84 |
| 4,985,074 | 1/1991 | Okada et al. | 75/444 |
| 4,992,406 | 2/1991 | Mauldin et al. | 502/304 |
| 5,538,703 | 7/1996 | Flytzani-Stephanopoulos et al. | 423/230 |

FOREIGN PATENT DOCUMENTS

| | | |
|---|---|---|
| 089587 | 9/1983 | European Pat. Off. . |
| 110357 | 6/1984 | European Pat. Off. . |
| 117496 | 9/1984 | European Pat. Off. . |
| 207645 | 1/1987 | European Pat. Off. . |
| 261870 | 3/1988 | European Pat. Off. . |
| 810253 | 3/1981 | U.S.S.R. . |

OTHER PUBLICATIONS

"Atomistic Interpretation of the Mechanism of Solid State Reactions and of Sintering" by W. A. Weyl; *Ceramic Age*; vol. 60, Part 51; pp. 28–38; ©1952.

"Zinc Oxide: Properties and Applications" by Harvey E. Brown; International Lead Zinc Research Organization, Inc. and Zinc Institute, Inc.; pp. 22; ©Jun., 1986.

*Primary Examiner*—Bekir L. Yildirim
*Attorney, Agent, or Firm*—Fay, Sharpe, Beall, Fagan, Minnich & McKee

[57] ABSTRACT

The surface area of a zinc oxide composition is increased, and stabilized to heating, by incorporation of a tri or tetravalent metal especially aluminium or gallium, e.g. in the form of a spinel with the zinc oxide. The composition is preferably made by coprecipitation of zinc and a compound of said metal and then calcination. The zinc oxide composition may also incorporate a Group VIII metal and be used as a catalyst for a Fischer Tropsch process.

10 Claims, No Drawings

ZINC OXIDE COMPOSITION FOR USE IN CATALYSTS

This is a continuation of application Ser. No. 08/446,786, filed May 26, 1995, now abandoned which is a national filing of PCT/GB93/02479, filed Dec. 2, 1993.

This invention concerns oxide compositions, in particular zinc oxide ones, and their use in catalysts.

Zinc oxide is used in catalysts as a support for catalytically active metals such as cobalt in Fischer Tropsch catalysts (see e.g. our EP 261870, the disclosure of which is hereby incorporated by reference). One problem with it is that it suffers shrinkage and sintering on heating to high temperatures, which may be those of the catalyst use or its regeneration. This shrinkage happens progressively with time and results in loss of activity.

We have discovered that the copresence of a trivalent or tetravalent metal, especially aluminium in a zinc oxide composition of high surface area can increase the surface area of the zinc oxide and/or reduce the loss of surface area on long term heating. Cobalt containing catalysts supported on said composition can be of high activity with good retention of that activity in spite of prolonged heating in use and/or regeneration.

The present invention provides a zinc oxide composition, which after calcination at 300° C for 5hr has a surface area of at least 30 $m^2/g$, said composition comprising at least one trivalent or tetravalent metal other than one of Group VIII of the Periodic Table, said metal being in atomic percentage to the zinc of 1–15%, and in the form of metal and/or metal oxide and/or a compound thermally decomposable thereto and/or a compound e.g. a spinel with the zinc oxide. There is also provided a method of increasing the surface area of a zinc oxide composition, which after calcination at 300° C. for 5 hr has a surface area of less than 30 $m^2/g$, which method comprises incorporating into said composition at least one such metal in the percentage and form as specified above; this increase can occur before but especially occurs after the composition has been heated to 500° C. for 10 hr.

There is also provided a precursor for the zinc oxide composition of this invention which comprises (i) at least one of precipitated zinc oxide and a zinc compound thermally decomposable to zinc oxide, and (ii) at least one compound of said trivalent or tetravalent valent-metal, said compound being a precipitated oxide or a compound thermally decomposable to an oxide of said metal or said zinc compound and said metal compound being thermally decomposable to a compound of zinc and said metal e.g. a spinel, and said metal being in atomic percentage to zinc as specified above. The precursor may be converted to the zinc oxide composition of the invention by heating (calcination) for example as described further below in relation to zinc oxide.

The present invention also provides a catalyst composition comprising cobalt on zinc oxide support, wherein said zinc oxide support is a zinc oxide composition of the invention. There is also provided a method of performing a Fischer Tropsch reaction to convert a mixture of carbon monoxide and hydrogen to hydrocarbons which comprises passing under Fischer Tropsch conditions said mixture over said cobalt containing catalyst composition after reductive activation.

The zinc oxide may be made by precipitation from an aqueous solution of a soluble zinc salt, such as zinc nitrate or chloride, by mixing with a weak base, such as ammonium hydroxide, carbonate or bicarbonate, or a tetraalkylammonium hydroxide or an organic primary, secondary or tertiary amine, at a temperature of 0° C. to the boiling point, usually at less than 50° C. such as 0°–50° C., and usually at pH5.5–8.5 followed by separation of the zinc hydroxide and/or carbonate precipitate, e.g. by filtration, then washing, e.g. with water, especially deionised water, to remove extraneous soluble ions, drying, e.g. at 100°–200° C. and then usually heating (calcination), e.g. in an inert atmosphere or an atmosphere comprising molecular oxygen, such as nitrogen or air, at 200°–600° C. for 6–1 hours such as 3 hr at 300° C. to produce the zinc oxide. This zinc oxide may itself have a surface area, determined by BET measurements with nitrogen (as are all surface areas herein), of at least 20 $m^2/g$, such as 40–80 $m^2/g$.

The trivalent and tetravalent metals may be non transition metals or lanthanide metals or transition metals, especially those of Groups IIIA, IVA, VA, VIA, VIIA, IB and IIB of the Periodic Table; as used in this specification the Periodic Table is that given in "Advanced Inorganic Chemistry" by F. A. Cotton and G. Wilkinson, J. Wiley, N.Y., 4th Ed. 1980. Preferably the metal is trivalent and is of Group IIIB of the Periodic Table, especially gallium or indium but most particularly aluminium, but may be manganese, chromium, vanadium, cerium or lanthanum. Examples of tetravalent metals are titanium, germanium, molybdenum tungsten and cerium. The invention will be particularly described with reference to aluminium but corresponding processes adapted as necessary may be used for the other trivalent or tetravalent metals.

The Aluminium may be present in the zinc oxide composition, following impregnation with aluminium of the above zinc oxide, whether in the form before or after calcination, or coprecipitation of aluminium with the zinc oxide. In the impregnation route, the above zinc oxide may be treated with an aqueous or organic solution of an aluminium compound, especially a thermally decomposable one, such as aluminium nitrate or a carboxylate such as an alkanoate, such as acetate or naphthenate or a dicarbonyl complex such as acetyl acetonate; preferably there is used an anhydrous solution in an organic solvent, such as an alkanol, e.g. of 1–6 carbons, such as methanol or ethanol or a ketone, such as a dialkylketone, e.g. of 3–6 carbons such as acetone or an ether such as a dialkylether, e.g. of 4–8 carbons, such as diethyl ether or a cyclic ether, e.g. of 4–8 carbons such as tetrahydrofuran, or a liquid paraffin hydrocarbon. The impregnation may be by the incipient wetness technique. After impregnation, the residual water or solvent is evaporated to leave an impregnated solid which is an example of the above specified precursor, and which is usually calcined, e.g. as described above. Preferably however the aluminium is incorporated by coprecipitation. The precipitation technique described above for production of zinc oxide may be modified by the presence of a water soluble aluminium salt, such as the nitrate, chloride or another as described above, in the aqueous solution of zinc salt before mixing with the weak base, e.g. to pH 5.5–10, followed by precipitation, washing, drying and calcining as before. The precipitation or impregnation of the zinc oxide and the zinc oxide composition may be performed in a batch or continuous manner and preferably with agitation, e.g. stirring and especially with maintenance of the pH at 5.5–10 such as 5.5–7.5. Preferably an aqueous solution of the zinc salt and an aqueous solution of the water soluble aluminium salt (or other one of said metal salts), are added continuously to an agitated aqueous solution of said weak base while keeping the pH at 5.5–10 especially 5.5–8.5 to produce a coprecipitate which is separated. Preferably the zinc salt and aluminium (or salt of said other metal) are premixed so the aqueous solution added to the base contains both salts.

The zinc oxide composition of the invention, after calcination e.g. in air at 300° C. for 5hrs, has a surface area of at least 30 m$^2$/g, preferably at least 80 m$^2$/g, e.g. 30–200 or 80–150 m$^2$/g. At least some (and preferably substantially all) the trivalent metal, especially aluminium, is usually present in the zinc oxide composition in the form of a spinel, whose presence can be determined by X-ray crystallography, so preferably the composition comprises a mixture of zinc oxide and said spinel.

The atomic amount of the trivalent or tetravalent metal is 0.4–15% (relative to the zinc in the zinc oxide composition), preferably 0.5–10% such as 0.9–6% especially 1.4–5%. The weight amount of trivalent or tetravalent metal especially aluminium or gallium in the zinc oxide composition is 0.5–7.5% by weight (as metal expressed by weight of zinc oxide), particularly 0.7–5% and is especially 0.8–2%. Amounts of the metal especially expressed as aluminium as oxide, may be 1.0–15% e.g. 1.5–10% and especially 1.6–4% by weight.

The zinc oxide composition may be made as above in the form of a powder, e.g. of 1–100 microns average diameter, but preferably for use as a catalyst support it is in the form of granules, e.g. of 100–1000 microns average diameter. The granules may be made, optionally after wetting of powder with water or solvent, by compression and granulation and sieving; the powder may be the calcined product made as above, but preferably the powder is the dried product before calcination, so that the calcination is performed on the granulated product. The zinc oxide compositions of the invention are usually of higher compression strength than those without the extra trivalent or tetravalent metal.

The zinc oxide composition of the invention, especially after calcination under conditions as described before, may be used as catalyst supports, in particular as supports for one or more Group VIII metals, e.g. nickel or preferably iron, but especially cobalt for use in Fischer Tropsch processes. In the compositions of the invention, the Group VIII metal may be present as an oxide and/or a compound thermally decomposable thereto. The use of cobalt will be described further, but the other Group VIII metals may be used instead. The cobalt is dispersed in the zinc oxide compositions of the invention which may be in the form of the powder, but preferably as granules. The dispersion may be substantially throughout the zinc oxide composition solid or substantially only at its surface. The dispersion may be achieved in a manner known per se for dispersion of cobalt onto catalyst supports, especially zinc oxide catalyst supports, e.g. as described in EP 261870, usually but not by coprecipitation of cobalt with the zinc and trivalent or tetravalent metal e.g. aluminium. The former dispersion may be achieved by immersion of the zinc oxide composition solid in a solution of the cobalt compound; the solution is preferably in an organic solvent, e.g. as described above. The cobalt compound, when supported on zinc oxide, is thermally decomposable to a cobalt oxide. It may be an inorganic salt, e.g. cobalt nitrate or a carboxylate, preferably an alkanoate, e.g. with 1–18 carbons in the alkanoate group such as acetate or octanoate or naphthenate, or a co-ordination complex such as a carbonyl or an organic di-carbonyl complex such as with acetylacetonate. The surface dispersion of cobalt on the zinc oxide composition may be achieved by spray coating the composition with a solution of the cobalt compound with evaporation of the solvent, e.g. by spraying the solution onto the solid composition at a temperature of at least 100° C. The coating may be performed a sufficient number of times to build upt the desired cobalt level and to the desired depth of impregnation. After the impregnation, the impregnated zinc oxide composition is usually dried, e.g. at 100°–250° C., followed by calcination, e.g. by heating at 250°–600° C. for 1–8 hrs e.g. at 400° C. for 2–4hrs.

The cobalt containing zinc oxide composition can have 1–300% Group VIII metal (expressed in g. atoms of metal on the basis of the moles of zinc oxide in the composition), in particular 2–200% and especially 5–70% such as 10–30%. The composition may contain 3–40%, e.g. 3–25% of the Group VIII metal (as metal on the basis of the total weight of the composition). If desired, a promoter or promoters may also be present, e.g. Zr, Ti, Ru and/or Cr and these are preferably impregnated in the zinc oxide composition, especially coimpregnated with the cobalt or other Group VIII metal. The catalyst compositions containing at least one Group VIII metal are preferably substantially free from alkali metal and alkaline earth metal, such as calcium, and are thus usually substantially free of calcium cements, e.g. calcium aluminates. Preferably however the catalyst compositions contain the Group VIII metal, especially cobalt as substantially the only transition metal, and especially consist substantially essentially of Zn and O atoms and of atoms of the trivalent or tetravalent metal, and atoms of the Group VIII metal especially cobalt.

The catalyst compositions of the invention containing the Group VIII metal or metals may be used in a Fischer Tropsch reaction in a manner known per se for Group VIII catalysts in said reaction. Generally, the catalyst, after granulation, compression or pelletization and crushing, is treated by passing over it a mixture of hydrogen and carbon monoxide, especially in a molar ratio of 0.5– 6:1, e.g. 1.5–2.5:1 or 1.7–2.5:1, such as synthesis gas. The reaction may be performed in a fixed bed, fluidised bed or slurry phase reactor or a two or three phase fluidised bed reactor, and may be a batch semi-continuous or continuous operation. It may be performed under an elevated pressure, e.g. of 0.1–10 MPa, such as 1–5 MPa and at an elevated temperature, e.g. of 160°–350° C., preferably 180°–250° C. especially 185°–210° C. The gas hourly space velocity GHSV for continuous operation is usually at least 100, e.g. 100–25000 hr$^{-1}$ especially 500–10,000 hr$^{-1}$. Before use in the process, the catalyst is usually activated to form at least some Group VIII metal (or lower valency metal oxide) by reduction with hydrogen or a hydrogen rich mixture with carbon monoxide (all optionally diluted with nitrogen) for example at a temperature of 150°–500° C, e.g. 200°–300° C. for a period of at least 5hrs such as 5–24 hrs. The activation may involve heating to the above temperatures first in an inert atmosphere, e.g. of nitrogen and then, preferably after cooling, heating in the reducing atmosphere. The Fischer Tropsch process is particularly selective to produce hydrocarbons, especially with at least 5 carbons such as 5–60 carbons and in particular waxes. The process can have conversions of carbon monoxide and of hydrogen each of at leat 50% especially at least 60% and selectivities to hydrocarbons of at least 3 carbons of at least 70% especially at least 80%, and to hydrocarbons of at least 5 carbons of at least 60% e.g. at least 70%. The selectivities to carbon dioxide and $C_2$ hydrocarbons are each preferably below 1.5%, while the selectivity to methane is usually less than 10% such as 5–10%. After use, the catalyst can be regenerated, e.g. by heating at 300°–600° C., e.g. 400°–600° C. in the presence of a gas comprising molecular oxygen, and may then be reductively activated as described above.

The catalyst compositions have high initial surface area, usually substantially the same as for the zinc oxide compositions and have, after heating for 10 hours, such as 10–60 hours, at 500° C., e.g. during regeneration or activation, a surface area of at least 30 m$^2$/g such as 30–60, or especially 40–60 m$^2$/g.

The zinc oxide composition of the invention may also be used with, and optionally as a support for, a copper containing catalyst, e.g. with 0.5–10%wt copper, for use in the conversion of carbon monoxide and hydrogen (e.g. in molar ratio of 1:1.5–2.5 such as 1:2) to methanol, e.g. at 0.1–10 MPa pressure, 150°–300° C. such as 180°–260° C. and a GHSV of 1000–60,000/hr, optionally in the presence of carbon dioxide. While the copper may be impregnated onto the zinc oxide composition of the invention, preferably the copper (eg as oxide or hydroxide) is co-precipitated with the zinc (eg as oxide, hydroxide or carbonate).

The invention is illustrated in the following Examples.

EXAMPLE 1

Zinc nitrate hexahydrate (182.8 g) and aluminium nitrate nonahydrate (3.49 g) were dissolved in deionised water (0.46 $dm^3$) and pumped at 50 $cm^3$ $min^{-1}$ into a rapidly stirred solution of ammonium bicarbonate (291.5 g) dissolved in deionised water (2.31 $dm^3$) to give a suspension at pH 7–8. The white co-precipitate was filtered and washed once by slurrying with deionised water (3.0 $dm^3$) for 30 minutes. The slurry was refiltered, and the white filter cake dried overnight (16 h) at 120° C. in air to leave a zinc oxide composition containing 0.5% Al (expressed as Al by weight of zinc oxide). X-ray diffraction on the composition showed the presence of zinc oxide and $ZnAl_2O_4$ (gahnite, a spinel in significant amounts).

EXAMPLE 2

The process of Example was repeated but with about double the amount of aluminium nitrate nonahydrate (namely 7.02 g). The product was a zinc oxide composition containing 1.0% aluminium (expressed as Al by weight of zinc oxide).

EXAMPLE 3

The process of Example 2 was repeated but with the aluminium nitrate replaced by gallium nitrate hexahydrate (1.835 g) to give a zinc oxide compositions containing 0.82 mol % gallium (based on moles of ZnO).

EXAMPLE 4

The effect of heat on the surface areas of the compositions of Examples 1–3 were tested initially (after heating in air for 3 hrs at 300° C.) and then after subsequently heating at 500° C. for 5, 24 and 60 hrs. The surface area was determined by BET measurements with nitrogen. The results were compared with those on a zinc oxide Composition (A) made as in Example 1 but without the aluminium.

| | Surface Area ($m^2/g$) | | | |
|---|---|---|---|---|
| Composition | Initially | After 5 hrs | After 24 hrs | After 60 hrs |
| A | 55 | 14 | | <5 |
| Example 1 | 84 | 52 | 37 | 34 |
| Example 2 | 104 | 62 | 52 | 47 |
| Example 3 | 58 | 22 | 21 | 19 |

The products of Ex 1–3 had a higher compression strength than that of Composition A.

EXAMPLE 5

Cobalt nitrate nonahydrate (54.9 g) dissolved in deionised water (200 $cm^3$) was slowly added to the powder of the composition of Example 1 (100 g) which had previously been calcined in air at 300° C. for 3 hrs. The slurry/powder obtained was throughly mixed, and then dried overnight at 90° C. in air. The dry powder was ground to <500 microns, and calcined in air by increasing the temperature at a rate of 100° C. per hour to 400° C., at which it was kept for 3 hrs. The resulting powder was pressed to form tablets under a pressure of 9 tonnes which were crushed and then the crushed granules sieved to 250–500 microns. The product was a catalyst composition B containing 10% cobalt (as Co, based on the weight of the composition of Example 1).

EXAMPLE 6

The catalyst composition B (10 $cm^3$:13.58 g) was loaded into a microreactor and reduced in hydrogen at atmospheric pressure with the temperature increased at a rate of 2° C. $min^{-1}$ to 300° C., which temperature was then held for 10 hrs. The reactor was then cooled to less than 60° C. and syngas ($CO:H_2$ in a molar ratio of 2.07:1, plus 20% nitrogen) was introduced to the reactor. The pressure in the reactor was increased to 30 bar, and the applied temperature increased slowly to 180° C. The temperature was then increased in small increments until >70% CO conversion was attained and Periodic mass balances were carried out to check the conversion and productivity. The average applied and bed temperatures were 197°–8° C. at least after 73 hrs when the conversion was 73.08% and productivity to $C_5$ hydrocarbons was 117.49 g/lbed/hr, and after 140.1 hrs when the conversion was 67.48% and the productivity to $C_{5+}$ hydrocarbons was 111 g/lbed/hr.

EXAMPLES 7 AND 8

The process of Example 3 was repeated with two levels of gallium nitrate addition, namely 4.62 g and 2.32 g (for Example 7 and 8 respectively) to give zinc oxide compositions containing 2.06 mol % and 1.0 mol % Ga (based on mols of ZnO). The surface area of the compositions and the effect of heat thereon was determined as in Example 4.

| | Surface Area $m^2/g$ | | |
|---|---|---|---|
| Composition | Initially | After 24 hrs | After 60 hrs |
| Example 7 | 94 | 49 | 47 |
| Example 8 | 88 | 36 | 31 |

COMPARATIVE EXAMPLES (i) The cobalt impregnation process of Example 5 was repeated using the composition A (zinc oxide without added aluminium) with a different amount of cobalt to give catalyst composition C containing 16% cobalt (as Co, based on the weight of the zinc oxide). The surface area of the cobalt impregnated product was determined as described in Ex. 4 before and after heating. The conditions of heating and results were as follows.

| Surface Area | Composition C |
|---|---|
| Surface Area $m^2/g$ | |
| Product | — |
| after 6 hr calcination at 300° C. | 136 |
| after 60 hr calcination at 500° C. | 13 |

-continued

| Surface Area | Composition C |
|---|---|
| Particle size (micron) of product as made | 250–500 |

(ii) Composition C was tested in the Fischer Tropsch process under conditions similar to those described in Ex 6 and the productivity of $C_{5+}$ hydrocarbons was determined.

The results were as follows, compared to those in Ex 6: the relative productivity means the percentage of the productivity after the longer hours on stream to the productivity after the shorter hours.

|  | Composition C | | Example 6 | |
|---|---|---|---|---|
| Hours in stream | 160 | 310 | 73 | 140 |
| Relative Productivity | 100 | 77 | 100 | 95 |

The Composition of Ex 6 also had a higher compression strength than that of Composition C.

I claim:

1. A zinc oxide composition, which after calcination at 300° C for 5 hr. has a surface area of at least 30 m²/g, said composition comprising at least one trivalent or tetravalent metal other than one of Group VIII of the Periodic Table, said metal being in atomic percentage to the zinc of 0.9–6%, and in the form of metal and/or metal oxide and/or a compound thermally decomposable thereto, and/or a compound with said zinc oxide, and said zinc oxide composition being such that in the absence of said trivalent or tetravalent metal and after calcination at 300° C. for 5 hr. it has a surface area of less than 30 m²/g.

2. A composition according to claim 1 wherein said metal is one of Group IIIB the Periodic Table.

3. A composition according to claim 2 wherein said metal is aluminium or gallium present at least partly in the form of a spinel with said zinc oxide.

4. A composition according to claim 1, said composition including said at least one trivalent or tetravalent metal, which has a surface area of 80–150 m²/g after calcination at 300° C. for 5 hr.

5. A composition according to claim 1 wherein the atomic percentage of said metal to zinc is 1.4–5%.

6. A composition according to claim 1 wherein said trivalent or tetravalent metal is selected from the group consisting of gallium, indium, manganese, chromium, vanadium, cerium, lanthanum, titanium, germanium, molybdenum, tungsten, and mixtures thereof.

7. A method of increasing the surface area and/or reducing the loss of surface area on long term heating of a zinc oxide composition, which after calcination at 300° C. for 5 hr. has a surface area of less than 30 m²/g, which method comprises incorporating into said composition at least one trivalent or tetravalent metal other than one of Group VIII of the Periodic Table, said metal being in atomic percentage to the zinc of 0.9–6% and in the form of metal and/or metal oxide and/or a compound thermally decomposable thereto, and/or a compound with said zinc oxide, to form a composition, which after calcination at 300° C. for 5 hr. has a surface area of at least 30 m²/g.

8. A catalyst composition comprising a Group VIII metal or copper with a zinc oxide composition which after calcination at 300° C. for 5 hr. has a surface area of at least 30 m²/g, said zinc oxide composition comprising at least one trivalent or tetravalent metal other than one of Group VIII of the periodic Table, said metal being in atomic percentage to the zinc of 0.9–6%, and in the form of metal and/or metal oxide and/or a compound thermally decomposable thereto, and/or a compound with said zinc oxide, and said zinc oxide composition being such that in the absence of said trivalent or tetravalent metal and after calcination at 300° C. for 5 hr. it has a surface area of less than 30 m²/g, said Group VIII metal being impregnated onto said zinc oxide composition.

9. A composition according to claim 8, which comprises cobalt impregnated onto said zinc oxide composition.

10. A composition according to claim 9 wherein said trivalent or tetravalent metal is aluminum or gallium present at least partly in the form of a spinel with said zinc oxide.

* * * * *

UNITED STATES PATENT AND TRADEMARK OFFICE
CERTIFICATE OF CORRECTION

PATENT NO. : 5,811,365
DATED : September 22, 1998
INVENTOR(S) : NAY, Barry

It is certified that error appears in the above-identified patent and that said Letters Patent is hereby corrected as shown below:

ON THE TITLE PAGE:

Item [75]

delete "Nay Barry" and insert therefor: ---Barry Nay---.

Signed and Sealed this

Thirteenth Day of June, 2000

Attest:

Q. TODD DICKINSON

*Attesting Officer*        *Director of Patents and Trademarks*